United States Patent
Suchan et al.

(10) Patent No.: US 8,747,114 B2
(45) Date of Patent: Jun. 10, 2014

(54) SET FOR PRODUCING A TEMPORARY TOOTH CROWN OR BRIDGE

(75) Inventors: Matthias Suchan, Hachenburg (DE); Alexander Bublewitz, Herborn (DE); Jens-Peter Reber, Meinerzhagen (DE)

(73) Assignee: Kettenbach GmbH & Co. KG, Eschenburg (DE)

( * ) Notice: Subject to any disclaimer, the term of this patent is extended or adjusted under 35 U.S.C. 154(b) by 505 days.

(21) Appl. No.: 11/388,941

(22) Filed: Mar. 24, 2006

(65) Prior Publication Data

US 2006/0228675 A1    Oct. 12, 2006

(30) Foreign Application Priority Data

Apr. 11, 2005    (DE) .......................... 10 2005 016 763

(51) Int. Cl.
*A61C 5/08*    (2006.01)

(52) U.S. Cl.
USPC .............................................. 433/219

(58) Field of Classification Search
USPC ........ 246/16, 19, 20; 264/16, 19, 20, 17, 222, 264/479, 494, 496; 433/37, 41–48, 219; 523/109, 115; 249/54; 425/2
See application file for complete search history.

(56) References Cited

U.S. PATENT DOCUMENTS

| | | | |
|---|---|---|---|
| 4,380,435 A | 4/1983 | Raeder et al. | |
| 4,553,936 A | 11/1985 | Wang | |
| 4,867,682 A | 9/1989 | Hammesfahr | |
| 5,403,885 A | 4/1995 | Voigt et al. | |
| 5,753,781 A * | 5/1998 | Oxman et al. | 525/415 |
| 5,769,633 A * | 6/1998 | Jacobs et al. | 433/37 |
| 5,856,373 A * | 1/1999 | Kaisaki et al. | 522/25 |
| 6,084,004 A | 7/2000 | Weinmann et al. | |
| 6,114,409 A | 9/2000 | Krebber | |
| 6,652,281 B1 | 11/2003 | Eckhardt et al. | |
| 2002/0081546 A1* | 6/2002 | Tricca et al. | 433/6 |
| 2003/0198914 A1* | 10/2003 | Brennan et al. | 433/9 |
| 2004/0038171 A1* | 2/2004 | Jacobs et al. | 433/37 |
| 2004/0044164 A1* | 3/2004 | Engelbrecht | 528/15 |
| 2004/0214140 A1* | 10/2004 | Fischer et al. | 433/215 |
| 2004/0241609 A1* | 12/2004 | Jia et al. | 433/167 |
| 2005/0042576 A1 | 2/2005 | Oxman et al. | |
| 2006/0183080 A1* | 8/2006 | Nosov et al. | 433/215 |

FOREIGN PATENT DOCUMENTS

| | | |
|---|---|---|
| DE | 36 23 276 | 1/1988 |
| DE | 42 17 115 | 12/1993 |
| DE | 691 01 702 | 7/1994 |
| EP | 0 566 221 | 2/1991 |
| EP | 0 522 341 | 6/1992 |
| EP | 0 678 282 | 10/1995 |

(Continued)

*Primary Examiner* — Todd Manahan
*Assistant Examiner* — Matthew Nelson
(74) *Attorney, Agent, or Firm* — McDonnell Boehnen Hulbert & Berghoff LLP

(57) ABSTRACT

A set or assembly for producing at least one temporary crown or bridge material has a carrier for accommodating a crown and bridge material and a crown and bridge material in an amount that is at least sufficient for the production of a tooth crown. The crown and bridge material is a light-curing and, in particular, flowable single-component material, and the carrier that can be adapted to the tooth situation is transparent or translucent. In another aspect, a method for producing a temporary tooth crown or bridge and a temporary tooth crown or bridge produced by the method are also provided.

2 Claims, 2 Drawing Sheets

Time and Work Step Schematic of a Light-Curing Temporary crown and Bridge Material

(56) References Cited

FOREIGN PATENT DOCUMENTS

| | | |
|---|---|---|
| EP | 0 687 451 | 12/1995 |
| EP | 0 897 710 | 9/2000 |
| EP | 0 738 137 | 2/2004 |
| EP | 1 173 137 | 12/2004 |
| WO | WO 93/13727 | 7/1993 |
| WO | WO 02/080802 | 10/2002 |

* cited by examiner

SET FOR PRODUCING A TEMPORARY TOOTH CROWN OR BRIDGE

CROSS REFERENCE TO RELATED APPLICATIONS

Applicant claims priority under 35 U.S.C. §119 of German Application No. 10 2005 016 763.2 filed Apr. 11, 2005.

BACKGROUND OF THE INVENTION

1. Field of the Invention

The present invention relates to a set for producing at least one temporary tooth crown or bridge, having a carrier for accommodating a crown and bridge material in an amount that is at least sufficient for the production of a tooth crown.

2. The Prior Art

In dental medicine, such temporaries are used to protect the soft tissue of the tooth (pulpa) from thermal, chemical, and bacterial influences, after the tooth has been prepared, i.e. ground down for the production of crowns or bridges. Furthermore, these temporaries serve a variety of functions. They maintain chewing function, fix the occlusal and/or sagittal jaw relationships in place, and they prevent the adjacent mucous membrane from growing onto the tooth stump. In the front tooth sector, in particular, such temporaries also fulfill esthetic and phonetic functions.

For the production of a temporary crown or bridge, an impression of the existing tooth situation is generally taken before preparation. After preparation of the tooth or teeth, the situation impression is then filled with an autopolymerizable temporary crown and bridge material, in the places of the prepared teeth. The filled impression is then repositioned on the prepared tooth stumps, and the temporary crown and bridge material is cured in the mouth, until an elastic phase has been reached. During this elastic phase, the material is removed and worked on, if necessary, before it is cured, either within the mouth, or outside of the mouth, with additional heating, for example. Such a material is described in EP 1 173 137 B1, for example.

During final curing outside of the mouth, the temporary crown or bridge shrinks, whereby the lumen formed in the temporary crown or bridge by means of the prepared tooth stump also shrinks. As a result, it is frequently necessary to enlarge the lumen of the temporary crown or bridge before attaching it to the prepared tooth stump. For example, the lumen of the temporary crown or bridge may be enlarged by grinding it down. Furthermore, it takes a comparatively long time until such autopolymerizing temporary crowns or bridges have reached their final technical properties, so that they can be subjected to full chewing stress. As a result, not only is the treatment time increased, but also the patient cannot put full stress on the temporary crown or bridge for at least several hours afterwards.

In EP 0 897 710 B1, a light-induced cationically curing composition is proposed, which can be used for plastics for temporaries or for prosthetic teeth. This composition contains camphor quinone and aromatic amines as initiators, for example. Furthermore, a light-curing plastic for temporary crowns and bridges is known under the designation "GC REVOTEK LC" from the company GC GERMANY GmbH. This material has a putty-like (putty) consistency. In producing a temporary crown or bridge, the material is first manually pre-shaped outside the mouth, then applied to the prepared tooth stump, and there roughly shaped by having the patient bite down on the material. After a first curing step using a light-curing lamp, the roughly shaped temporary crown or bridge is removed from the patient's mouth and cured further by applying more light extraorally. Subsequently, the shape is corrected with a polisher.

Although this method is particularly labor-intensive for the dentist, the temporary crowns or bridges obtained in this manner provide only an insufficient reproduction of the original tooth situation. Such temporary crowns or bridges therefore feel uncomfortable in the mouth. Furthermore, the production of a temporary crown or bridge with a putty-like material is disadvantageous, since its flow properties are insufficient, so that the material does not optimally adapt to the tooth contours. When these known materials are used in an impression, there is the risk that the impression will be plastically or elastically deformed due to straining, so that again, only an insufficient reproduction of the original tooth situation is possible.

Furthermore, there are two-component systems and dual-curing two-component systems that cure purely chemically, such as LUXATEMP® SOLAR, a temporary dental material from the company DMG, or PROVIPONT®, a temporary dental material from the company Vivadent Ivoclar, which can be additionally cured by supplying light, after chemical curing. These two-component systems must be precisely metered and mixed well with one another before use, because otherwise, curing is negatively influenced. Therefore such two-component systems are often perceived as being disadvantageous.

Fundamentally, it is difficult for a dentist, when using the known materials for temporary crowns or bridges, to remove them from the mouth after the first adaptation on the prepared tooth stump, at the right moment so that they can be worked. In the case of chemical curing initiated by mixing a base component with a catalyst component, this curing process proceeds continuously. In this connection, the temporary crown or bridge must remain in the patient's mouth until it can be removed in one piece, without tearing or undergoing any other plastic deformations. At the same time, excess amounts of the material, which have run into undercuts, for example (e.g. interstices between the teeth), must still be elastically deformable. Otherwise, the temporary can be removed only with difficulty after it has cured completely. In autopolymerizing systems, the right point in time for first removal of the temporary and subsequent finishing cannot be clearly determined.

For the production of a quickly curing impression, a transparent impression tray is proposed in U.S. Pat. No. 4,867,682, which is filled with an impression material that can be polymerized by means of light. This light-polymerizing impression material has the elasticity required for impression materials after final curing, in order to guarantee easy removal from the mouth. In contrast, significantly greater values for modulus of elasticity and bending strength are required for a temporary crown and bridge material. The known light-polymerizing impression material is consequently completely unsuitable for use as a crown and bridge material (compare ISO 4823 for impression materials and ISO 10477 for crown and bridge materials). Furthermore, in EP 0 522 341, a transparent material is described that has great hardness and low elastic deformation, for the production of a bite registration. This material is completely unsuitable as an impression material, because of its great hardness.

SUMMARY OF THE INVENTION

It is therefore an object of the present invention to provide a set and a method for producing temporary tooth crowns or bridges of the type stated initially, as well as such tooth crowns or bridges, which is particularly easy for the user to handle during production, and allows an improved impression of the original tooth situation.

These and other objects are accomplished, according to one aspect of the invention, essentially by a set or assembly in which the crown and bridge material is a light-curing single-component material, and the carrier that can be adapted to the tooth situation is transparent or translucent. In the present case, light-curing is understood to mean photoactivation by means of radiation, particularly light in the visible wavelength range. The set according to the invention, for producing temporary tooth crowns or bridges, can be worked with in particularly simple manner, since the material for the temporary does not have to be mixed from different components before being processed. Furthermore, a first curing phase until an elastic phase of the crown and bridge material is reached can be carried out by means of the light-curing, in which state the dental material can be removed from the mouth without tearing, so that it can be worked further.

Since the carrier is transparent or translucent, the light can be radiated in through the carrier. This feature makes it possible for the crown and bridge material to be cured by means of light directly on the stump in a carrier that can be adapted to the tooth situation. The crown and bridge material therefore cures quickly and in defined manner, cannot shrink into the free lumen, and is given a contour that essentially corresponds to the original tooth situation. The adaptation to the original tooth situation can take place by adapting the carrier itself accordingly as a thermoplastic film carrier. Alternatively, a transparent impression tray may be filled with a transparent impression material or the like, which then forms the carrier and is adapted to the original tooth situation in known manner. Complicated reworking of the temporary tooth crown or bridge is therefore not necessary in most cases of use.

An integral part of the set according to the invention is the carrier. The carrier accommodates the flowable, light-curing, single-component material, from which the temporary crown or bridge is formed, and at the same time serves as a shaper for this material. According to a preferred embodiment, the carrier is made of a transparent or translucent impression material that can be held in a transparent or translucent impression tray, for example. According to another preferred embodiment, the carrier of a transparent or translucent thermoplastic film.

If the carrier is formed by a transparent or translucent impression material, this material preferably has an opacity between 0 and 70%, preferably between 0 and 50%, at a layer thickness of 10 mm and at a wavelength between 350 nm and 700 nm. A particularly preferred range of the opacity at this layer thickness and wavelength lies between 0 and 30%, particularly between 0 and 20%. The opacity can be determined using a Minolta spectrophotometer CM-3500d in reflection, SCE, shutter diameter 30 mm in the opacity measurement mode, observation angle 10°, type of light D65. This opacity allows particularly good light curing of the crown and bridge material, while the material is accommodated in the impression material, without the light being absorbed or reflected by the impression material to any noteworthy extent.

In a further embodiment, the transparent impression material is a two-component addition-crosslinking or condensation-crosslinking silicone or cationically crosslinking aziridinopolyether or condensation-crosslinking alkoxysilyl polyether, or addition-crosslinking silyl polyether, or hydrocolloid or alginate. Preferably, an addition-crosslinking, transparent silicone impression material is used.

The impression material can be situated in an impression tray. This impression tray can be a full or partial tray or a dental tray available under the trade description DUAL ARCH/TRIPLE-TRAY® tray that can consist of plastic or metal. In a particularly preferred embodiment, the impression tray is transparent or translucent. The impression tray particularly demonstrates an opacity between 0 and 70%, preferably between 0 and 50%, particularly preferably between 0 and 30%, and very particularly preferably between 0 and 20%, particularly at a layer thickness of 5 mm and at a wavelength between 350 nm and 700 nm particularly between 370 nm and 550 nm.

According to another embodiment of the invention, the carrier is a thermoplastic film that is transparent or translucent at body temperature, and demonstrates an opacity between 0 and 70%, preferably between 0 and 50%, particularly preferably between 0 and 30%, and very particularly preferably between 0 and 20%, particularly at a layer thickness of 1 mm and at a wavelength between 350 nm and 700 nm, particularly between 370 nm and 550 nm.

In this connection, it is preferred if the thermoplastic film has a layer thickness between 0.1 mm and about 4 mm, and a softening temperature between about 40° C. and 80° C. This carrier demonstrates the advantage that its layer thickness is usually less than that of a carrier formed from impression material. As a result, better light curing can be achieved through the film carrier that can be produced directly in the patient's mouth. Furthermore, because of its small dimensions, the thermoplastic film carrier is more practical to handle in some cases of use.

The thermoplastic film from which the transparent or translucent thermoplastic film carrier for the set according to the invention can be produced preferably is made of ethyl vinyl acetate (EVA) or polycaprolactone (Capa). This material demonstrates sufficient strength and at the same time good light permeability.

To produce a temporary crown or bridge, the crown and bridge material and the carrier and/or the impression tray are preferably coordinated with one another in such a manner that the crown and bridge material is initiated through the carrier and/or the impression tray, in a first exposure step, at least until an elastically deformable phase of the crown and bridge material has been reached, intraorally, by means of light supplied from outside the carrier or impression tray or both. After the elastically deformable phase of the crown and bridge material has been reached, it can be removed from the patient's mouth without permanent deformation and without tearing. At the same time, excess amounts of the crown and bridge material, which have run into undercuts, for example, can be removed before they cure in the mouth to such an extent that removal would then be possible only with great effort.

It is preferred if the crown and bridge material can be completely cured intraorally, by means of light. For this purpose, the temporary tooth crown or bridge is repositioned on the prepared tooth stump again, in its elastically deformable phase, and light is applied to it there. In this way, shrinkage of the lumen of the temporary tooth crown or bridge can be prevented to such an extent that no additional grinding is necessary before it is glued or cemented in. In some cases of use, it is actually possible that because of the lumen shrinkage, the temporary crown or bridge already adheres so tightly to the prepared tooth stump that no additional attachment of the temporary is necessary.

According to a preferred embodiment of the invention, the carrier of the set according to the invention and/or the impression tray can be provided with at least one substance that blocks light of a defined wavelength and/or intensity range. The crown and bridge material and the carrier, with or without impression tray, can consequently be coordinated with one another in such a manner that in the first exposure step, the crown and bridge material can be cured by means of light supplied from outside the carrier and/or the impression tray only until the elastically deformable state is reached.

Therefore, if the light application period is slightly exceeded, this excess period does not yet result in complete curing of the crown and bridge material inside the mouth, which might make it very difficult to remove again. In the production of a temporary crown or bridge, there is therefore the certainty that the crown and bridge material is always removed from the mouth in its elastically deformable phase, after the light has acted on it sufficiently, as long as it is surrounded by the carrier, with or without impression tray. The final curing can then take place by means of another application of light, with light of the same or a different wavelength and/or intensity. This final curing of the light-curing temporary crown and bridge material can take place either in the carrier (with or without impression tray) or outside of the carrier, for example directly on the stump.

The crown and bridge material according to the invention can be a single-component dental material, which has a modulus of elasticity (measured analogous to ISO 10477) between 1 MPa and 50 MPa during the elastically deformable phase. Preferably, the modulus of elasticity is between 2 MPa and 45 MPa, particularly preferably between 2 MPa and 35 MPa, and very particularly preferably between 2 MPa and 25 MPa. In this connection, the crown and bridge material is preferably adjusted so that the elastically deformable phase lasts at least 15 s, particularly between 15 s and 90 s. In this way, residue-free removal of the crown and bridge material in its elastically deformable phase can be achieved even in the case of slight undercuts. Shape stability that is sufficient for processing can be achieved as well.

The crown and bridge material according to the invention is preferably a cationically curable single-component material that preferably contains cationically polymerizable epoxy resins and/or oxetanes, a photoinitiator system that allows cationic polymerization in the visible range, particularly aryl iodonium salts or aryl iodonium salt in combination with camphor quinone and/or amines, or preferably a radically curing single-component material that preferably has at least one methacrylate monomer and/or polymer having at least two methacrylate groups.

Before exposure, the temporary crown and bridge material according to the invention is preferably plastically deformable and capable of flow. In this plastically deformable phase, the temporary crown and bridge material can have a viscosity between 10 and 100,000 Pa·s, preferably between 10 and 10,000 Pa·s, particularly preferably between 20 and 1,000 Pa·s, and very particularly preferably between 20 and 600 Pa·s, and/or a consistency between 50 and 15 mm, preferably between 50 and 18 mm, particularly preferably between 47 and 21 mm, and very particularly preferably between 45 and 24 mm.

The temporary crown and bridge material according to the invention can be cured completely, in a second exposure step, until a duroplastic material state is reached. In the duroplastic material state, the material preferably has a modulus of elasticity of greater than or equal to 1,000 MPa, preferably greater than or equal to 2,000 MPa, particularly preferably greater than or equal to 2,500 MPa, and very particularly preferably greater than or equal to 3,000 MPa, and/or a bending strength greater than or equal to 90 MPa, preferably greater than or equal to 100 MPa, and particularly preferably greater than or equal to 110 MPa.

According to the invention, the elastically deformable phase is reached because in a first exposure step, only part of the exposure period and/or exposure intensity that would actually be required for complete curing of the temporary crown and bridge material is radiated in. Surprisingly, it has been shown that only part of the photoinitiator is activated by the light radiated in during the first exposure step, and generates radicals and is used up in this manner. Because only part of the photoinitiator generates radicals, only part of the methacrylate and epoxy oligomers is polymerized. In this manner, a marked elastically deformable phase is generated. This elastically deformable phase lasts for a period of longer than 15 s, preferably longer than 30 s, particularly longer than 45 s, particularly preferably longer than 60 s. Likewise, it has surprisingly been shown that the remaining, unused photoinitiator amount remains uninfluenced by the first irradiation, i.e. is not damaged, and is therefore available for final curing to a duroplastic state, in a second exposure step. To better check complete through-curing of the temporary, it is particularly advantageous that a color change from an intensive yellow tone to a lighter color can be observed by means of the use of camphor quinone.

To produce a temporary tooth crown or bridge, according to the invention, first a transparent or translucent dental tray or impression of at least one untreated tooth is produced using an impression tray. This dental tray or impression is then filled with a crown and bridge material and repositioned on at least one ground-down tooth. The plastically deformable crown or bridge material accommodated in the dental tray or impression is subsequently cured with light, until the crown and bridge material has reached an elastically deformable phase. This phase preferably lasts between 15 s and 90 s, and, according to a preferred embodiment, is defined by a recovery of more than 90% and/or a modulus of elasticity (measured analogous to ISO 10477) between 1 MPa to 50 MPa, preferably between 2 MPa to 45 MPa, particularly preferably between 2 MPa to 35 MPa, and very particularly preferably between 2 MPa to 25 MPa. The crown and bridge material can then be adapted and/or worked extraorally, in its elastically deformable phase.

The final curing of the crown and bridge material again takes place intraorally, by means of light, on at least one ground-down tooth, or extraorally, until the crown and bridge material reaches its cured, duroplastic phase, and has a modulus of elasticity of greater than or equal to 1,000 MPa and a bending strength greater than or equal to 90 MPa. Preferably the modulus of elasticity is greater than or equal to 2,000 MPa, particularly preferably greater than or equal to 2,500 MPa, and very particularly preferably greater than or equal to 3,000 Mpa. Preferably the bending strength is greater than or equal to 100 MPa, and particularly preferably greater than or equal to 110 MPa. To improve the fit accuracy, intraoral curing on the prepared tooth stump is preferred, whereby the crown and bridge material no longer needs to be accommodated in an impression or tray. In contrast, the crown and bridge material is more easily accessible extraorally, in part.

A transparent or translucent carrier can be produced as follows. First, a thermoplastic film is heated to a temperature that lies below 80° C. and above the softening temperature of the thermoplastic film, and then is applied to the patient's mouth together with an impression tray charged with a kneadable material. The thermoplastic film can be placed against at least one untreated tooth in this heated state, and can be adapted by means of the kneadable material, if necessary. The thermoplastic film remains placed against the at least one untreated tooth, forming a carrier, until the thermoplastic film has cooled down to a temperature below the softening temperature. The impression tray, the kneadable material, and the dental tray formed from the thermoplastic film can then be removed from the mouth.

The invention furthermore relates to a temporary tooth crown or bridge that is produced according to one of the methods described above. These temporary tooth crowns or bridges are characterized by very great fit accuracy and good reproduction of the original tooth situation. Furthermore, such temporary tooth crowns or bridges can be produced in particularly user-friendly manner.

BRIEF DESCRIPTION OF THE DRAWING

Other objects and features of the present invention will become apparent from the following detailed description considered in connection with the accompanying drawing. It should be understood, however, that the drawing is designed for the purpose of illustration only and not as a definition of the limits of the invention.

In the drawing.

DETAILED DESCRIPTION OF PREFERRED EMBODIMENTS

Figure 1:
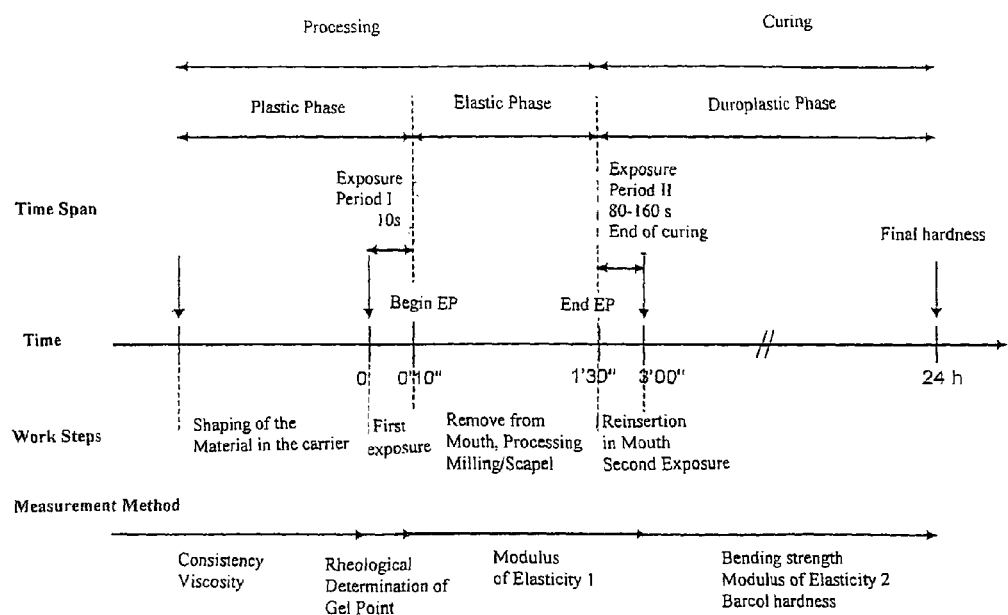
FIG. 1 is a schematic representation depicting the time and work steps of a light-curing temporary crown and bridge material.
Figure 2:
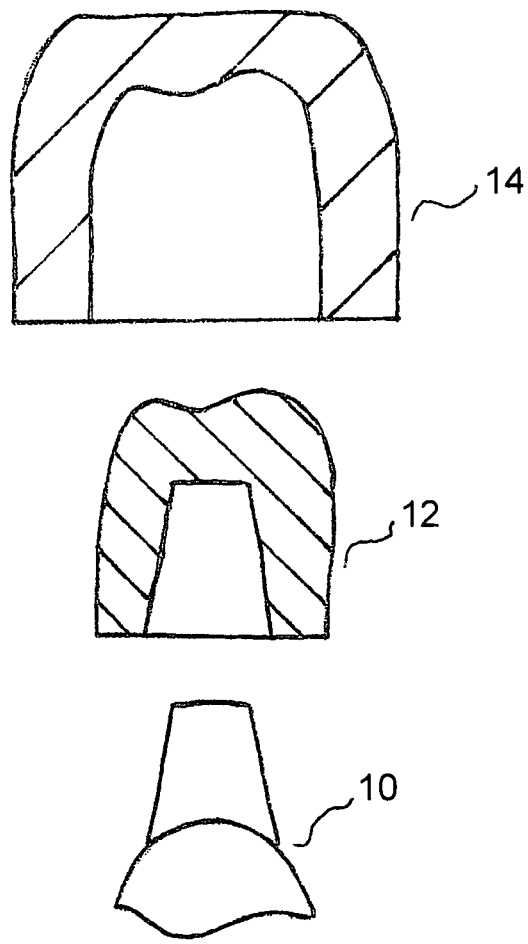
FIG. 2 in an exploded view of a gingiva with prepared tooth stump with a temporary tooth crown or bridge made from dental material and an impression tray or carrier for producing the temporary crown or bridge in accordance with an embodiment of the invention.

In the following, the invention will be described making reference to two examples and the schematic representation of FIG. 1 from which the work steps and time spans of the production of a temporary tooth crown or bridge 12 shown in FIG. 2 from the assembly or set according to the invention, i.e. according to the method according to the invention are evident. In this connection, the set is made up of the light-curing single-component material, a transparent or translucent impression material, or a transparent or translucent thermoplastic film material as the carrier, and an impression tray 14, if necessary.

Example 1

The patient has a tooth gap in the side tooth region of the right upper jaw, which is supposed to be closed with a bridge. For this purpose, the hard tooth substance of the teeth that delimit the gap must first be worn away, to accommodate the bridge columns, according to dental guidelines (preparation).

Before preparation, an impression of the teeth is taken, using a transparent impression material that was filled into a transparent impression tray (e.g. VITA® single-use impression tray), so that the impression forms a carrier. In this way, the original outer contour of the teeth has been recorded. To connect the two impressions, a crosspiece between the two bridge columns, made of the impression material, can be cut out.

After preparation, the impressions of the prepared teeth 10 and the crosspiece that was cut out are filled, in the impression, with the plastically deformable, flowable, and light-curing single-component material, and the impression is put back into the mouth. In this connection, the material, which is still plastically deformable, is given the shape of the prepared tooth 10 towards the inside, and the original outer contour of the teeth towards the outside, by means of the shaped carrier 14. After a first exposure of the single-component material through the transparent carrier 14, the material reaches its elastically deformable phase. In this state, the temporary 12, which is still elastic, is removed from the mouth and rough-finished. In this connection, it is important that all excess material that has flowed into undercuts is removed.

The temporary, worked on in this manner, can now be set back onto the tooth stumps, either in the carrier or without the carrier, and cured by means of a second exposure, by pressing a button, until the material has reached a duroplastic state. If necessary, it is possible to remove the temporary again, in order to carry out the final finishing, for example polishing. Subsequently, the temporary bridge is attached to the tooth stumps with a temporary attachment cement.

In this example, instead of a transparent impression tray that is frequently suitable only for taking an impression of one jaw, a so-called "dual-arch impression tray" can be used, the upper and lower part of which, for the upper and lower jaw, are generally separated only by a gauze, at the height of the chewing level. In this way, exposure of the light-curing single-component material from the chewing side is possible without hindrance.

Example 2

The patient has a deeply destroyed tooth in the left lower jaw, the outer contour of which is still more or less maintained with a filling, and which is supposed to be provided with a crown. Here again, preparation of the tooth is necessary. Before the preparation, an impression of the existing contour of the tooth is taken, using a transparent thermoplastic film.

For this purpose, the film, which has been brought to a plastically deformable state by means of heating it above its softening temperature, is molded onto the tooth either manually or using a kneadable material. After the film has cooled to below its softening temperature, the film is now removed from the mouth and the kneadable material is removed from the film, if applicable. The film shaped in this manner now serves as a carrier for shaping the temporary crown.

The other work steps are not directly comparable to Example 1, whereby in this case, of course, no crosspiece is present.

Although only a few embodiments of the present invention have been shown and described, it is to be understood that many changes and modifications may be made thereunto without departing from the spirit and scope of the invention as defined in the appended claims.

What is claimed is:

1. A method for producing a temporary tooth crown or bridge comprising the following steps:
   (a) creating a transparent or translucent dental tray or an impression of at least one untreated tooth using an impression tray;
   (b) filling the dental tray or impression with a dental material and repositioning the dental tray or impression on at least one intra-oral ground-down tooth;
   (c) curing the dental material within the dental tray or impression with light in a first exposure step until the dental material reaches an elastically deformable phase defined by a modulus of elasticity of the dental material measured analogous to ISO 10477 between 1 MPa and 50 MPa;
   (d) conducting extraoral adaptation or working of the dental material while in the elastically deformable phase, an (e) curing the dental material with light on at least one ground-down tooth or tooth model until the dental material reaches a cured phase to form the temporary tooth crown or bridge; and
(f) detaching the temporary tooth crown or bridge from the transparent or translucent dental tray or impression after production and fixing the temporary crown or bridge to a tooth stump or adjacent teeth;
wherein before the first exposure step, the dental material has a plastically deformable phase with a viscosity between 10 and 100,000 Pas or a consistency measured analogous to ISO 4823 between 50 and 15 mm.

2. The method according to claim 1, wherein the transparent or translucent dental tray is produced by means of the following steps:
  (a) heating a thermoplastic film to a temperature that lies below 80° C. and above the softening temperature of the thermoplastic film;
  (b) applying the thermoplastic film to a patient's mouth, with an impression tray charged with a kneadable material;
  (c) applying the thermoplastic film to at least one untreated tooth to form a dental tray, for a time span until the thermoplastic film has cooled down to a temperature below the softening temperature; and
  (d) removing the impression tray, the kneadable material, and the dental tray formed from the thermoplastic film from the patient's mouth.

* * * * *